United States Patent [19]

Schwarzenbach et al.

[11] 4,012,360

[45] Mar. 15, 1977

[54] BIS-SALICYLOYL-DICARBOXYLIC ACID DIHYDRAZIDES AS STABILIZERS FOR POLYOLEFINES

[75] Inventors: Kurt Schwarzenbach, Aesch; Helmut Mueller, Binningen; Siegfried Rosenberger, Riehen, all of Switzerland

[73] Assignee: Ciba-Geigy Corporation, Ardsley, N.Y.

[22] Filed: Aug. 6, 1975

[21] Appl. No.: 602,499

Related U.S. Application Data

[63] Continuation of Ser. No. 421,467, Dec. 3, 1973, abandoned, which is a continuation of Ser. No. 170,379, Aug. 9, 1971, abandoned.

[52] U.S. Cl. .................. 260/45.9 NC; 260/559 H; 260/471 R
[51] Int. Cl.[2] ..................................... C07C 103/26
[58] Field of Search ............... 260/559 H, 45.9 NC, 260/471 R

[56] References Cited

UNITED STATES PATENTS

| | | | |
|---|---|---|---|
| 2,765,304 | 10/1956 | Siegrist et al. | 260/307 |
| 3,511,834 | 5/1970 | Siegrist et al. | 260/559 |
| 3,549,572 | 12/1970 | Minigawa | 260/558 |
| 3,600,383 | 8/1971 | Atkinson et al. | 260/307 |
| 3,734,885 | 5/1973 | Muller et al. | 260/45.9 NC |
| 3,806,358 | 4/1974 | Glander et al. | 260/45.9 NC |

FOREIGN PATENTS OR APPLICATIONS

41-1940 10/1966 Japan

*Primary Examiner*—Arthur P. Demers
*Attorney, Agent, or Firm*—Luther A. R. Hall

[57] ABSTRACT

New bis-salicyloyl-dicarboxylic acid dihydrazides are stabilizers for polyolefines. They are prepared by reacting a salicylic acid hydrazide with a dicarboxylic acid chloride or a dicarboxylic acid diester.

9 Claims, No Drawings

BIS-SALICYLOYL-DICARBOXYLIC ACID DIHYDRAZIDES AS STABILIZERS FOR POLYOLEFINES

This is a continuation of application Ser. No. 421,467, filed on Dec. 3, 1973, which in turn is a continuation of application Ser. No. 170,379, filed on Aug. 9, 1971, both now abandoned.

The subject of the present invention are new bissalicyloyl dicarboxylic acid dihydrazides as well as their use for the stabilisation of polyolefines.

Because of their physical and electrical properties, polyolefines, especially polypropylene, are very suitable for use as an insulating material in the electrical industry, especially for the sheathing and coating of copper wires, copper cables and other electrically conducting materials made of copper. Unfortunately, however, the said good properties of the polyolefines are worsened through the fact that in contact with transition metals, especially with copper and its compounds, the polyolefins suffer an oxidative degradation catalysed by these metals. Additions of copper of less than 1%, for example, already lead to the stability to oxidation of polypropylene being lowered by a factor of about 100.

Various acylation products from dicarboxylic acids and nitrogen bases, such as, for example, amides of oxalic acid, especially oxanilides, as well as dihydrazides of various dicarboxylic acids, are already known for the stabilisation of polyolefines against the harmful action of transition metals.

All these compounds show certain technical disadvantages. On the one hand, their activity is in no case sufficiently great to suppress the harmful action of the transistion metal completely. On the other hand, they objectionably discolour the polyolefine either already during incorporation or under thermo-oxidative ageing conditions. The latter disadvantage, in particular, manifests itself in the case of another class of active dicarboxylic acid dihydrazide derivatives which has been disclosed, namely in the case of the bis-arylidine-dicarboxylic acid dihydrazides. Whilst these display a satisfactory deactivator action, they are already inherently yellow-coloured compounds. None of the types of compounds hitherto disclosed combines within itself the technically desired optimum stabilising action with absence of colour under use conditions.

It has now been found, surprisingly, that the compounds of the formula I

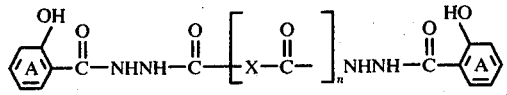

in which X denotes a direct bond, an alkylene radical with 1 to 8 carbon atoms, phenylene radical or a naphthylene radical and n denotes 0 or 1, and the rings A are unsubstituted or one ring A or both rings A are substituted by alkyl groups, alkenyl groups, cycloalkyl groups, aralkyl groups, further hydroxyl groups, alkoxy groups, acyloxy groups, acylamino groups or halogen, preferably by 1 or 2 alkyl groups with 1–18 carbon atoms, 1 or 2 groups with 3–4 carbon atoms, 1 or 2 groups with 6–8 carbon atoms, 1 or 2 benzyl groups, 1 or 2 α-methylbenzyl groups, a further hydroxyl group, an alkoxy group with 1–18 carbon atoms, an acyloxy group with 2–18 or an acylamino group with 2–18 carbon atoms, and 1 or 2 chlorine atoms, are very suitable for stabilising homopolymeric or copolymeric polyolefines, especially against thermo-oxidative degradation, and that these compounds at the same time possess good colour properties.

The compounds of the formula I protect homopolymeric and copolymeric polyolefines especially against thermooxidative degradation in the presence of transition metals.

The compounds which can be used according to the invention are not only excellent stabilisers, the action of which clearly surpasses that of the classes of compounds described above, but additionally have the advantage of being colourless. This permits their incorporation into polyolefines without objectionably discolouring the latter. All above-mentioned previously known compounds have the property of causing discolouration in polyolefines under ageing conditions, whilst the compounds according to the invention under these conditions cause practically no discolourations, which represents a great technical advantage for long-term stabilisation.

X in formula I can, for example, be an alkylene radical with 1 to 8 carbon atoms, such as methylene, ethylene, propylene, butylene, trimethylbutylene, pentylene, hexylene or octylene. It can also denote a phenylene radical, such as the 1,3- or 1,4-phenylene radical, or a naphthylene radical, such as the 2,6- or 1,4-naphthylene radical. The rings A can each be substituted by 1 or 2 alkyl groups with, preferably, 1 to 8 carbon atoms, such as, for example, methyl, ethyl, propyl, iso-propyl, butyl, sec.-butyl, tert.-butyl, amyl, tert.-amyl, sec.-amyl, hexyl, iso-heptyl, octyl, tert.-octyl, sec.-nonyl and dodecyl. The rings A can also each be substituted by 1 or 2 alkenyl groups with, preferably, 3 or 4 carbon atoms, such as, for example, allyl or butenyl, or 1 or 2 cycloalkyl groups with, preferably, 6 to 8 carbon atoms, such as, for example, cyclohexyl, α-methylcyclohexyl or cyclooctyl. If the substituent of the rings A is an alkoxy group with, preferably, 1 to 18 carbon atoms, this group can, for example, be methoxy, ethoxy, propoxy, butoxy, hexoxy, octoxy, decyloxy, dodecyloxy, tetradecyloxy or octadecyloxy. The rings A can furthermore each be substituted by an acyloxy group, preferably with 2 to 18 carbon atoms, or an acylamino group, preferably with 2 to 18 carbon atoms and the acyl radicals of the following acids, for example, can be involved: acetic acid, propionic acid, butyric acid, isobutyric acid, valeric acid, caproic acid, 2-ethylcaproic acid, caprylic acid, capric acid, lauric acid, myristic acid, palmitic acid, stearic acid, acrylic acid, methacrylic acid, crotonic acid, oleic acid, benzoic acid and phenylacetic acid.

The compounds of the formula I in which X denotes the direct bond, an alkylene radical with 3 to 8 carbon atoms, a phenylene radical or a naphthylene radical and n denotes 0 or 1 and the rings A can be unsubstituted or each substituted by 1 or 2 alkyl groups with 1 to 8 carbon atoms, an alkoxy group with 1 to 18 carbon atoms or chlorine, are particularly preferred.

As metal deactivators, those compounds of the formula I are particularly preferred, in which X denotes an alkylene radical with 3 to 8 carbon atoms and n denotes 0 or 1 and the rings A are unsubstituted or in which X denotes the direct bond and n denotes 1 and the rings A are each substituted by 1 or 2 alkyl groups with 1 to 8 carbon atoms and/or an alkoxy group with 1 to 8 carbon atoms and/or an alkoxy group with 1 to 8 carbon atoms.

As antioxidants, those compounds of the formula I are particularly preferred in which X denotes the direct bond, an alkylene radical with 3 to 8 carbon atoms or a phenylene radical and n denotes 1, and the rings A are each substituted by 1 or 2 alkyl groups with 4 to 8 carbon atoms or an alkoxy group with 1 to 18 carbon atoms.

Particularly good stabilising properties as metal deactivators are shown, for example, by the following compounds of the formula I: N,N'-bis-salicyloyl-oxalic acid dihydrazide, N,N'-bis-(2-hydroxy-5-tert.butyl-benzoyl)-oxalic acid dihydrazide N,N'-bis-(2-hydroxy-4-octoxy-benzoyl)-oxalic acid dihydrazide, N,N'-bis-salicyloyl-adipic acid dihydrazide and N,N'-bis-salicyloyl-sebacic acid dihydrazide. Particularly good stabilising properties as antioxidants are shown, for example, by the following compounds of the formula I: N,N'-bis-(2-hydroxy-3,5-di-tert.butyl-benzoyl)-adipic acid dihydrazide, N,N'-dis-(2-hydroxy-3,5-di-tert.butyl-benzoyl)-terephthalic acid dihydrazide, N,N'-bis-(2-hydroxy-5-tert.butyl-benzoyl)-terephthalic acid dihydrazide, N,N'-bis-(2-hydroxy-4-methoxybenzoyl)-sebacic acid dihydrazide, N,N'-bis-(2-hyroxy-4-octoxybenzoyl)-oxalic acid dihydrazide, N,N'-bis-(2-hydroxy-4-octoxybenzoyl)sebacic acid dihydrazide, N,N'-bis-(2-hydroxy-3,5-di-tert.butyl-benzoyl)-oxalic acid dihydrazide, N,N'-bis-(2-hydroxy-4-methoxy-benzoyl)-oxalic acid dihydrazide and N,N'-bis-(2-hydroxy-4-methoxy-benzoyl)-trimethyladipic acid dihydrazide.

The compounds of the formula I protect polyolefines against degradation, preferably α-olefin polymers, such as polypropylene, optionally crosslinked polyethylene, polyisobutylene, polymethylbutene-1, polymethylpentene-1, polybutene-1, polyisoprene and polybutadiene; copolymers of the monomers on which the said homopolymers are based, such as ethylene-propylene copolymers, propylene-butene-1 copolymers, propylene-isobutylene copolymers, styrene-butadiene copolymers, and terpolymers of ethylene and propylene with diene, such as, for example, hexadiene, dicyclopentadiene or ethylidenenorbornene; mixtures of the above-mentioned homopolymers, such as, for example mixtures of polypropylene and polyethylene, polypropylene and polybutene-1 or polypropylene and polyisobutylene. Polypropylene, as well as its mixtures and the copolymers which contain propylene units, are preferred.

The compounds of the formula I are incorporated into the substrates in a concentration of 0.01 to 5% by weight calculated relative to the material to be stabilised. Preferably, 0.05 to 1.5, and especially preferably 0.1 to 0.8% by weight of the compounds, relative to the material to be stabilised, are incorporated into the latter.

The incorporation may be effected after the polymerisation, for example by mixing at least one of the compounds of the formula I, and further additives if desired, into the melt in accordance with the methods customary in the art, before or during shaping, or by application of the dissolved or dispersed compounds to the polymer, if necessary with subsequent evaporation of the solvent.

In the case of crosslinked polyethylene, the compounds are added before the crosslinking.

As further additives together with which the stabilisers usable according to the invention can be employed, there may be mentioned:

1. Antioxidants of the aminoaryl and hydroxyaryl series. In the case of the latter, the sterically hindered phenol compounds should be mentioned, for example: 2,2'-thiobis-(4-methyl-6-tert.butylphenol), 4,4'-thiobis-(3-methyl-6-tert. butylphenol), 2,2'-methylene-bis-(4-methyl-6-tert.butylphenol), 2,2'-methylene-bis-(4-ethyl-6-tert.butylphenol), 4,4'-methylene-bis-(2-methyl-6-tert.butylphenol), 4,4'-butylidene-bis-(3-methyl-6-tert.butylphenol), 2,2'-methylene-bis-[4-methyl-6-(α-methylcyclohexyl)-phenol], 2,6-di-(2-hydroxy-3-tert.butyl-5-methylbenzyl)-4-methyl-phenol, 2,6-di-tert.butyl-4-methylphenol, 1,1,3-tris-2-methyl-(4-hydroxy-5-tert.butyl-phenyl)-butane, 1,3,5-trimethyl-2,4,6-tri-(3,5-di-tert.butyl-4-hydroxy-benzyl)-benzene, esters of β-4-hydroxy-3,5-di-tert.butylphenylpropionic acid with monohydric or polyhydric alcohols, such as methanol, ethanol, octadecanol, hexanediol, nonanediol, thiodiethylene glycol, trimethylolethane or pentaerythritol, 2,4-bis-octylmercapto-6-(4-hyroxy-3,5-di-tert.butylphenoxy)-6-octylmercapto-s- triazine, 1,1,-bis-(4-hydroxy-2-methyl-5-tert. butyl-phenyl)-3-dodecyl-mercapto-butane, 4-hydroxy-3,5-di-tert. butylbenzyl-phosphonic acid esters, such as the dimethyl, diethyl or dioctadecyl ester, (3-methyl-4-hydroxy-5-tert.butylbenzyl)-malonic acid dioctadecyl ester, s-(3,5-dimethyl-4-hydroxyphenyl)-thioglycollic acid octadecyl ester, and esters of bis-(3,5-di-tert.butyl-4-hydroxybenzyl)-malonic acid, such as the didodecyl ester, the dioctadecyl ester and 2-dodecylmercaptoethyl ester.

Amongst the aminoaryl derivatives, aniline and naphthylamine derivatives as well as their heterocyclic derivatives should be mentioned, for example phenyl-1-naphthylamine, phenyl-2-naphthylamine, N,N'-diphenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2,-dihydroquinoline, monooctyliminodibenzyl and dioctyliminodibenzyl, and polymerised 2,2,4-trimethyl-1,2-dihydroquinoline, though in the case of the combined use of the compounds of the formula I with the above-mentioned amine compounds the stabilised polymer no longer possesses such good colour properties, because of the tendency to discolouration of the amine compounds.

2. UV-absorbers and light protection agents such as:
a. 2-(2'-Hydroxyphenyl)-benztriazoles, for example the 5'-methyl, 3',5'-di-tert.butyl, 5'-tert.butyl, 5-chloro-3', 5'-di-tert.butyl, 5-chloro-3'-tert.butyl-5'-methyl, 3',5'-di-tert.amyl, 3'-methyl-5'-β-carbomethoxyethyl, 5-chloro-3', 5'-di-tert.amyl derivative.

b. 2,4-Bis-(2'-hydroxyphenyl)-6-alkyl-s-triazines, for example the 6-ethyl or 6-undecyl derivative.

c. 2-Hydroxy-benzophenones, for example the 4-hydroxy, 4-methoxy, 4-octoxy, 4-decyloxy, 4-dodecyloxy, 4,2',4'-trihydroxy or 2'-hydroxy-4,4'-dimethoxy derivative.

d. 1,3-Bis-(2'-hydroxy-benzoyl)-benzenes, for examples 1,3-bis-(2'-hydroxy-4'-hexyloxy-benzoyl)-benzene, 1,3-bis-(2'-hydroxy-4'-octoxy-benzoyl)-benzene and 1,3-bis-(2'-hydroxy-4'-dodecyloxy-benzoyl)-benzene.

e. Aryl esters of optionally substituted benzoic acids, such as, for example, phenyl salicylate, octylphenyl salicylate, benzoylresorcinol, dibenzoylresorcinol, 3,5- di-tert.butyl-4-hydroxybenzoic acid 2,4-di-tert.butyl-phenyl ester or octadecyl ester.

f. Acrylates, for example α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, and N-(β-carbomethoxy-vinyl)-2-methylindoline.

g. Nickel compounds, for example nickel complexes of 2,2'-thiobis-(4-tert.octylphenol), such as the 1:1-and 1:2-complex, optionally with other ligands such as n-butylamine, nickel complexes of bis-(4-tert.octyl-phenyl)-sulphone, such as the 2:1-complex, optionally with other ligands such as 2-ethylcaproic acid, nickel dibutyldithiocarbamate, nickel salts of 4-hydroxy-3,5-di-tert.butylbenzyl-phosphonic acid monoalkyl esters, such as of the methyl, ethyl or butyl ester, and the nickel complex of 2-hydroxy-4-methyl-phenyl-undecylketonoxime.

h. Oxalic acid diamides, for example 4,4'-di-octylox-yanilide, 2,2'-di-octyloxy-5,5'-di-tert.butyl-oxanilide and 2,2'-di-dodecyloxy-5,5'-di-tert.butyl-oxanilide.

3. Phosphites, such as triphenyl phosphite, diphenylalkyl phosphites, phenyldialkyl phosphites, trinonylphenyl phosphite, trilauryl phosphite, trioctadecyl phosphite, 3,9-di-isodecyloxy-2,4,8,10-tetraoxa-3,9-diphosphaspiro-(5,5)-undecane and tri-(4-hydroxy-3,5-di-tert.butylphenyl) phosphite.

4. Nucleating agents, such as 4-tert.butylbenzoic acid, adipic acid and diphenylacetic acid.

5. Compounds which destroy peroxides, such as esters of β-thiodipropionic acid, for example the lauryl, stearyl, myristyl or tridecyl ester. Salts of 2-mercaptobenzimidazole, for example the zinc salt and diphenylthiourea.

6. Other additives, such as antistatic agents, flame-proofing agents, asbestos, glass fibres, kaolin, talc and blowing agents.

When using the stabilisers according to the invention in combination with phenolic antioxidants, particulary good stabilising effects are achieved if compounds which destroy peroxides, such as higher alkyl esters of thiopropionic acid are employed simultaneously, since these compounds which destroy peroxides not only, as is known, show a synergism with the phenolic antioxidants, but additionally with the stabilisers of the formula I.

The manufacture of the compounds which are usable according to the invention can above all be effected by two reaction paths which are in themselves known:

a. Reaction of 2 mols of a salicylic acid hydrazide, which is optionally substituted in the benzene nucleus, with one mol of a reactive derivative of a dicarboxylic acid, for example a dicarboxylic acid diester or a dicarboxylic acid dichloride, or b. Two-fold acylation of a dicarboxylic acid dihydrazide with a salicylic acid chloride which is optionally substituted in the benzene nucleus.

The polyolefines stabilised by the addition of the compounds according to the invention are in particular suitable for use as coating materials for copper wires and cable, but also for other types of metal coating, as well as for the manufacture of shaped articles, such as films, filaments, foils, pipes, injection-moulded articles and the like. They can also be used mixed with copper or with pigments containing copper.

The invention is explained in more detail in the examples which follow.

EXAMPLE 1

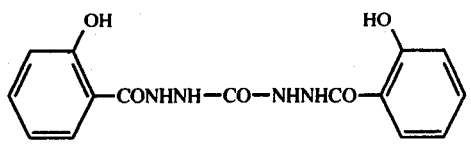

18 g. of carbohydrazide are suspended in 500 ml of dimethylacetamide and 62.4 g of salicyloyl chloride are added over the course of 45 minutes at 25°–45° C, whilst stirring. The homogeneously dissolved, yellowish-coloured reaction mixture is stirred for a further 45 minutes at room temperature and is then poured into 1 liter of water. The white, crystalline solid which hereupon precipitates is filtered off, washed with water and recrystallised from ethylene glycol monomethyl ether.

The N,N'-bis-(salicyloyl)-carbohydrazide thus obtained (Stabiliser No. 1) melts at 258° C.

EXAMPLE 2

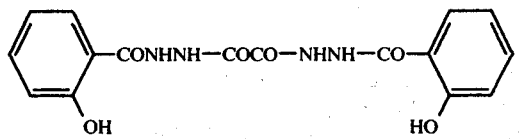

35.4 g of oxalic acid bis-hydrazide are suspended in 1000 ml of dimethyl acetamide, the suspension is briefly heated to 100° C and cooled to room temperature, and 93.5 g of salicylic acid chloride are slowly added in such a way that the reaction temperature does not exceed 40° C. After a further 15 minutes' stirring a largely homogeneous, yellowish solution has been obtained. After filtering off the undissolved constituents, the solution is mixed with 1.2 liters of ice water, whereupon the reaction product precipitates. The substance is filtered off, washed with water and purified by again precipitating it from dimethyl acetamide solution by means of water. After isolation and intensive drying at 130° C in vacuo, N,N'-bis-(salicyloyl)-oxalic acid dihydrazide (Stabiliser No. 2) is obtained as a white powder of melting point>320° C (decomposition).

If, in this example, the salicylic acid chloride is replaced by the equimolecular amount of one of the acid chlorides of Table 1 below, and the analogous procedure is followed, the corresponding N,N'-bis-acyl-oxalic acid dihydrazides, having the melting points indicated, are obtained:

Table 1

| Acid chloride | Melting point of the bis-salicyloyl-oxalic acid dihydrazide |
|---|---|
| (structure: 3-methyl-2-hydroxybenzoyl chloride) | 330° C (decomposition) (Stabiliser No. 3) |

Table 1-continued

| Acid chloride | Melting point of the bis-salicyloyl-oxalic acid dihydrazide |
|---|---|
| ![structure with OH, COCl, Cl] | 307° C (decomposition) (Stabiliser No. 4) |

EXAMPLE 3

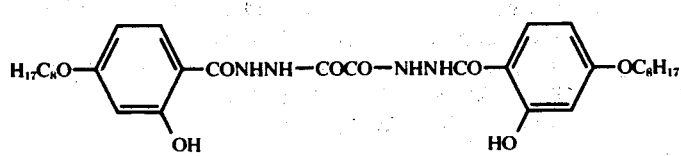

25 g of 2-hydroxy-4-octoxy-benzhydrazide and 5.7 g of oxalic acid dimethyl ester are dissolved in 200 ml of ethylene glycol monomethyl ether and the reaction mixture is heated to the boil for 15 hours. The reaction product separates out in the form of a white precipitate. After cooling, the product is filtered off, boiled with 100 ml of ethylene glycol monomethyl ether, filtered off hot and subsequently washed with methanol. After drying in vacuo at 100° C. N,N'-bis-(2-hydroxy-4-octoxybenzoyl)-oxalic dihydrazide (Stabiliser No. 5) is obtained in the form of a white powder of melting point 251° C.

If, in this example, 2-hydroxy-4-octoxy-benzhydrazide is replaced by the equimolecular amount of one of the hydrazides of Table 2 below, and the analogous procedure is followed, the corresponding N,N'-bis-salicyloyl-oxalic acid dihydrazides, having the melting points indicated, are obtained:

Table 2

| Hydrazide | Melting point of the bis-salicyloyl-oxalic acid dihydrazide |
|---|---|
| CONHNH₂, OH (ortho) | >320° C (decomposition), see Example 2 (Stabiliser No. 2) |
| CONHNH₂, OH, X | 318° C (Stabiliser No. 6) |
| CONHNH₂, OH, X, X | >300° C (Stabiliser No. 7) |

EXAMPLE 4

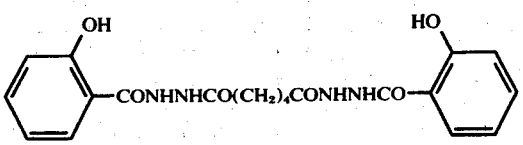

36.8 g of adipic acid dihydrazide are suspended in 500 ml of dimethylacetamide and 62.4 g of salicyloyl chloride are added at 25°–40° C over the course of 45 minutes, whilst stirring. The homogeneously dissolved, yellowish-coloured reaction mixture is stirred for a further 3 hours at room temperature and is then poured into 1 liter of water, whereupon a white, crystalline solid precipitates. The substance is filtered off, washed with water and recrystallised from ethylene glycol monomethyl ether.

The N,N'-bis-(salicyloyl)-adipic acid dihydrazide (Stabiliser No. 8) thus obtained melts at 252° C.

If, in the present example, the adipic acid dihydrazide is replaced by the equivalent amount of one of the dicarboxylic acid dihydrazides of Table 3 below and the analogous procedure is followed, the N,N'-bis-(salicyloyl)-dicarboxylic acid dihydrazides having the melting points indicated, are obtained:

Table 3

| Dicarboxylic acid dihydrazide | Melting point of the N,N'-bis-(salicyloyl)-dicarboxylic acid dihydrazide |
|---|---|
| CONHNH₂—(CH₂)₈—CONHNH₂ | 262° C (Stabiliser No. 9) |
| 1,4-phenylene bis-CONHNH₂ | 321° C (Stabiliser No. 10) |
| 1,3-phenylene bis-CONHNH₂ | 300° C (Stabiliser No. 11) |
| CONHNH₂—CH₂—CONHNH₂ | 258 – 262° C (Stabiliser No. 12) |

In the same way, reaction of a dicarboxylic acid dihydrazide with a suitably substituted 2-hydroxybenzoyl chloride yields the following compounds:

N,N'-Bis-(2-hydroxy-5-[α-phenylethyl]-benzoyl)-malonic acid dihydrazide (Stabiliser No. 13)

N,N'-Bis-(2-hydroxy-4-stearoyloxy-benzoyl)-sebacic acid dihydrazide (Stabiliser No. 14)

N,N'-Bis-(2-hydroxy-5-acetylamino-benzoyl)-adipic acid dihydrazide (Stabiliser No. 15)

N,N'-Bis-(2-hydroxy-5-stearoylamino-benzoyl)-oxalic acid dihydrazide (Stabiliser No. 16)

EXAMPLE 5

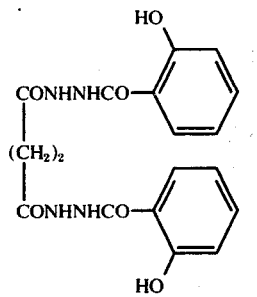

60 g of salicylic acid hydrazide are dissolved in 400 of dimethylacetamide and 42.0 g of succinic acid dichloride are added over the course of 60 minutes at 25°–40° C. A solution of 30 g of pyridine in 60 ml of dimethylacetamide is simultaneously added dropwise. The homogeneous, yellowish reaction mixture is stirred for one hour at 70° C and then poured into 5 liters of water, whereupon a white precipitate separates out. The substance is filtered off, washed with methanol and dried in vacuo at 90° C. For purification, the product is dissolved in 200 ml of dimethylacetamide, 2.5 liters of methanol and 2.5 liters of water are added, and the product is allowed to crystallise out over the course of 1 hour. The substance is dried in vacuo at 90° C. The N,N'-bis-(salicyloyl)-succinic acid dihydrazide (Stabiliser No. 17) thus obtained melts at 275° C.

EXAMPLE 6

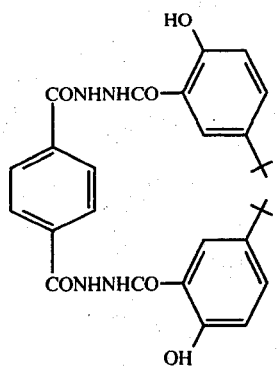

8.3 g of 2-hydroxy-5-tert.butyl-benzhydrazide are dissolved in 50 ml of dimethylacetamide and a solution of 4.0 g of terephthalic acid dichloride in 20 ml of dimethylacetamide is added over the course of 30 minutes at 20°–35° C. The homogeneous, yellowish reaction mixture is stirred for 2 hours at 65° C and then poured into 500 of water, whereupon a white precipitate separates out. The product is filtered off, washed with a little ethanol and recrystallised from dimethylformamide. The N,N'-bis-(2-hydroxy-5-tert.butyl-benzoyl)-terephthalic acid dihydrazide (Stabiliser No. 18) thus obtained melts at 330°–334° C.

EXAMPLE 7

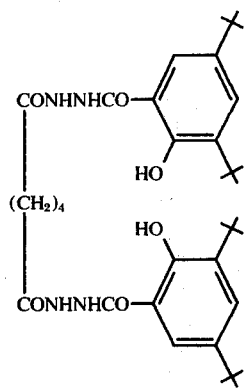

10 g of 2-hydroxy-3,5-di-tert.butyl-benzhydrazide are dissolved in 80 ml of dimethylacetamide and 3.5 of adipic acid dichloride are added over the course of 30 minutes at 20°–30° C. A solution of 3.0 g of pyridine in 10 ml of dimethylacetamide is simultaneously added dropwise. The homogeneous reaction mixture is stirred for 1 hour at 50° C and then poured into 500 ml of water, whereupon a white precipitate separates out. The substance is filtered off, washed with methanol and dried in vacuo at 100° C. The product can be recrystallised from diethylene glycol monomethyl ether (melting point 193° C). The N,N'-bis-(2-3,5-di-tert. butyl-benzoyl)-adipic acid dihydrazide (Stabiliser No. 19) thus obtained melts at 296°–298° C.

If, in this example, the adipic acid dichloride is replaced by the equivalent quantity of one of the dicarboxylic acid dichlorides of Table 4 below, and the analogous procedure is followed, the N,N'-bis-(2-hydroxy-3,5-di-tert.butylbenzoyl)-dicarboxylic acid hydrazides, having the melting points indicated, are obtained:

Table 4

| Dicarboxylic acid dichloride | Melting point of the N,N'-bis-(2-hydroxy-3,5-di-tert.butyl benzoyl)-dicarboxylic acid dihydrazide |
|---|---|
| COCl–(CH$_2$)$_8$–COCl | 235° C (see Example 8) (Stabiliser No. 20) |
| COCl–C$_6$H$_4$–COCl | 217° C (Stabiliser No. 21) |

EXAMPLE 8

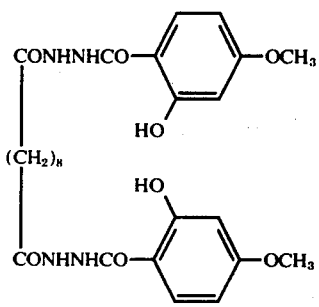

15 g of 2-hydroxy-4-methoxy-benzhydrazide are dissolved in 100 ml of dimethylacetamide and 9.8 g of sebacid acid dichloride are added over the course of 30 minutes at 20°–30° C. A solution of 6.5 g of pyridine in 20 ml of dimethylacetamide is simultaneously added dropwise. The homogeneous reaction mixture is stirred for one hour at 50° C and then poured into 500 ml of water, whereupon a white precipitate separates out. The substance is filtered off and dried in vacuo at 100° C. The product can be recrystallised from diethylene glycol monomethyl ether (melting point 193° C). The N,N'-bis-(2-hydroxy-4-methoxy-benzoyl)-sebacic acid dihydrazide (Stabiliser No. 22) thus obtained melts at 253°–254° C.

If, in this example, the 2-hydroxy-4-methoxy-benzhydrazide is replaced by the equimolecular amount of one of the hydrazides of Table 5 below, and the analogous procedure is followed, the corresponding N,N'-bis-acyl-dicarboxylic acid dihydrazides, having the melting points indicated, are obtained:

Table 5

| Hydrazide | Melting point of the bis-acyl-dicarboxylic acid dihydrazide |
|---|---|
| [structure: CONHNH₂, OH, with two X substituents on benzene ring] | 235° C (see Example 7) (Stabiliser No. 20) |
| [structure: CONHNH₂, OH, OC₈H₁₇ on benzene ring] | 202° C (Stabiliser No. 23) |

In the same way, reaction of a 2-hydroxy-4-alkoxybenzhydrazide with succinic acid dichloride yields the N,N'-bis'-(2-hydroxy-4-dodecyloxy-benzoyl)-succinic acid dihydrazide (Stabiliser No. 24) or N,N'-bis-(2-hydroxy-4-octadecyloxybenzoyl)-succinic acid dihydrazide (Stabiliser No. 25).

EXAMPLE 9

The compounds of Table 6 are each manufactured in accordance with the method of the example referred to in column 2:

Table 6

| Compound | Manufactured according to example | Melting point |
|---|---|---|
| [structure with CH₃O, OH, OCH₃, CONHNHCOCONHNHCO bridge, symmetric] | 3 | 298° C (Stabiliser No. 26) |
| [structure with OH, OC₈H₁₇, CONHNHCOCONHNHCO bridge, symmetric] | 3 | 280° C (Stabiliser No. 27) |
| [structure with OH, t-octyl groups, CONHNHCO—(CH₂)₄CONHNHCO bridge, symmetric] | 7 | 229° C (Stabiliser No. 28) |

Table 6-continued

| | Manufactured according to example | Melting point |
|---|---|---|
| 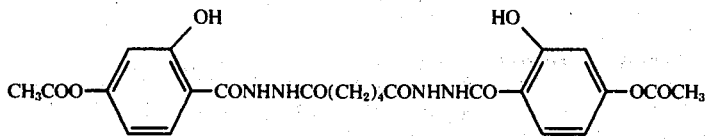 | 4 | 237–240° C (Stabiliser No. 29) |

N,N'-Bis-(2-hydroxy-4-acetoxy-benzoyl)-adipic acid dihydrazide is boiled for 2 hours in methylcellosolve with a three-fold molar amount of sodium hydroxide. After cooling, water is added, whereupon N,N'-bis-(2,4-dihydroxybenzoyl)-adipic acid dihydrazide (Stabiliser No. 30) precipitates.

EXAMPLE 10

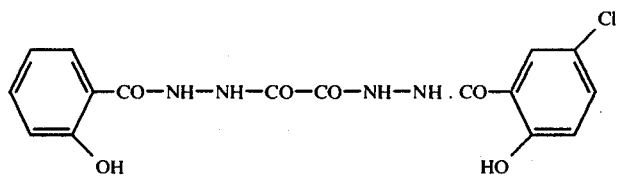

Stage I:

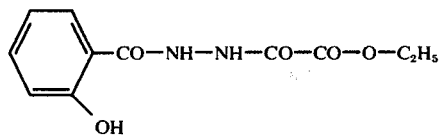

30.4 g of salicylic acid hydrazide are dissolved in 200 ml of dimethylacetamide and 20.0 g of triethylamine are added. The solution is cooled to 0° C and 27.3 g of oxalic acid monoethyl ester monochloride are added dropwise over the course of 30 minutes whilst stirring and cooling. A pale yellow, crystalline precipitate separates out in a strongly exothermic reaction. The reaction mixture is stirred for a further 2 hours at 50° C and is then poured into approx. 1 liter of cold water. The product is filtered off, washed with water and dried. Melting point: 202° C. The N-salicyloyl-N'-(ethoxyoxatyl)-hydrazine thus obtained is practically pure and does not have to be recrystallised.

Stage II:

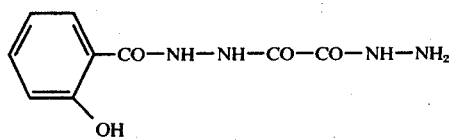

36.8 g of N-salicyloyl-N'-ethoxyoxalyl)-hydrazine from Stage I are suspended in 500 ml of ethanol and 15 g of hydrazine hydrate are slowly added at room temperature, whilst stirring. Thereafter the reaction mixture is warmed to 60° C for 2 hours, in the course of which the suspension becomes very voluminous.

The precipitate is filtered off and washed with water and ethanol.

After recrystallisation from ethylene glycol monomethyl ether, mono-(N-salicyloyl)-oxalic acid dihydrazide of decomposition point approx. 250° C is obtained.

Stage III:

23.8 g of mono-(N-salicyloyl)-oxalic acid dihydrazide from Stage II are dissolved in 700 ml of dimethylacetamide at 40° C, the solution is cooled to 15° C, and a solution of 19.1 g of 5-chlorosalicylic acid chloride in 30 ml of absorbed dioxane is added dropwise. Thereafter the reaction mixture is warmed to 60° C for a further 2 hours, clarified by filtration and poured into approx. 1.5 liters of ice water. The white, voluminous precipitate is filtered off, washed with water and spirit and recrystallised from dimethylformamide. The N-salicyloyl-N'-5-chlorosalicyloyl-oxalic acid dihydrazide (Stabiliser No. 31) thus obtained has a melting point of above 330° C.

The previously known metal deactivators for polyolefines which are listed in Table 7 below were conjointly tested as comparison compounds in the examples of tests which follow:

Table 7

| Stabiliser No. | Chemical designation |
|---|---|
| 32 | Oxanilide |
| 33 | Oxalic acid dihydrazide |
| 34 | Carbohydrazide |
| 35 | Malonic acid dihydrazide |
| 36 | Adipic acid dihydrazide |
| 37 | Terephthalic acid dihydrazide |
| 38 | Isophthalic acid dihydrazide |
| 39 | Succinic acid bis-phenylhydrazide |
| 40 | Sebacic acid bis-phenylhydrazide |
| 41 | Salicylic acid hydrazide |
| 42 | N-Acetyl-N'-salicyloyl-hydrazine |
| 43 | N-Salicyloyl-N'-salicylal-hydrazine |

EXAMPLE 11 a. Manufacture of the Test Specimens 100 parts of polypropylene (melt index 3.2 g/10 mins, 230° C/2160 g) are intensely mixed for 10 minutes in a shaking apparatus with 0.1 part of 3-(3,5-di-t.butyl-4-hydroxy-phenyl)-propionic acid octadecyl ester, 0.3 part of dilauryl thiodipropionate and 0.5 part of an additive listed in Table 8 below.

The mixture obtained is kneaded for 10 minutes in a Brabender plastograph at 200° C, 1.0% by weight of powdered copper (manufactured electrolytically, Merck) is then added, and the whole is intensely mixed for a further 2 minutes at the same temperature. The composition thus obtained is subsequently pressed in a platen press, at 260° C platen temperature, to give 1 mm thick sheets, from which 1 cm wide and 17 cm long strips are punched.

The heat-stabilised test specimens without addition of copper, or with addition of copper but without metal deactivator, which are required for comparison purposes, are manufactured analogously.

b. Testing

The activity of the metal deactivators added to the test strips containing copper is tested by heat ageing in a circulating air oven at 149° C and is compared with test strips not containing copper. For this purpose, 3 test strips of each formulation are employed. The incipient easily visible decomposition of the test strip is defined as the end point.

The preservation factor indicated in the 4th column of Table 8 is characterised as follows:

$$\text{Preservation factor} = \frac{\text{Days till decomposition occurs, with copper}}{\text{Days till decomposition occurs, without copper}} \times 100$$

Table 8

| Stabiliser No. | Days before decomposition starts | | Preservation factor |
|---|---|---|---|
| | without copper | with copper | |
| Without additive | 18 – 27 | <<1 | <1 |
| 1 | 17 | 12 | 70 |
| 2 | 30 | 26 | 86 |
| 5 | 30 | 26 | 86 |
| 6 | 32 | 23 | 72 |
| 7 | 38 | 32 | 84 |
| 8 | 20 | 18 | 90 |
| 9 | 29 | 24 | 82 |
| 12 | 20 | 18 | 90 |
| 19 | 30 | 19 | 63 |
| 21 | 27 | 17 | 63 |
| 22 | 28 | 17 | 60 |
| 27 | 28 | 16 | 57 |
| 31 | 29 | 21 | 73 |
| Comparison Products | | | |
| 32 | 18 | 1 | 6 |
| 33 | 24 | 6 | 25 |
| 36 | 18 | 2 | 11 |
| 37 | 25 | 2 | 8 |
| 39 | 21 | 1 | 5 |
| 40 | 25 | 14 | 56 |
| 41 | 27 | 8 | 30 |
| 42 | 20 | 4 | 20 |
| 43 | 19 | 16 | 84 |

EXAMPLE 12 a. Manufacture of the test specimens 100 parts of polypropylene (melt index 3.2 g/10 mins, 230° C/2160 g) are intensely mixed for 10 minutes in a shaking apparatus with 0.1 part of 3-(3,5-di-t.-butyl-4-hydroxy-phenyl)-propionic acid octadecyl ester, 0.3 part of dilauryl thiodipropionate and 0.5 part of an additive listed in Table 9 below.

The mixture obtained is kneaded for 10 minutes in a Brabender plastograph at 200° C, 1.0% by weight of powdered copper (manufactured electrolytically, Merck) is then added, and the whole is intensely mixed for a further 2 minutes at the same temperature. The composition thus obtained is subsequently pressed in a platen press, at 260° C platen temperature, to give 1 mm thick sheets, from which 1 cm wide and 17 cm long strips are punched by means of a punch tool.

The heat-stabilised test specimens without the addition of copper, or with addition of copper but without metal deactivator, which are required for comparison purposes, are manufactured analogously.

b. Testing

The activity of the metal deactivators added to the test strips containing copper is tested by heat ageing in a circulating air oven at 135° C and is compared with test strips not containing copper. For this purpose, 3 test strips of each formulation are employed. The incipient easily visible decomposition of the test strip is defined as the end point.

The preservation factor indicated in the 4th column of Table 9 is characterised as follows:

$$\text{Preservation factor} = \frac{\text{Days till decomposition occurs, with copper}}{\text{Days till decomposition occurs, without copper}} \times 100$$

Table 9

| Stabiliser No. | Days before decomposition starts | | Preservation factor |
|---|---|---|---|
| | without copper | with copper | |
| Without additive | 70 – 95 | <1 | <1 |
| 1 | 103 | 63 | 61 |
| 2 | 135 | 113 | 84 |
| 5 | 162 | 106 | 66 |
| 6 | 109 | 95 | 87 |
| 7 | 132 | 126 | 95 |
| 9 | 128 | 102 | 80 |
| 12 | 103 | 84 | 82 |
| 19 | 123 | 100 | 81 |
| 21 | 157 | 109 | 70 |
| 22 | 132 | 89 | 67 |
| 23 | 133 | 93 | 70 |
| Comparison products | | | |
| 34 | 76 | 13 | 17 |
| 35 | 72 | 1 | 1 |
| 37 | 88 | 4 | 5 |
| 41 | 90 | 24 | 27 |
| 42 | 90 | 27 | 30 |
| 43 | 86 | 72 | 84 |

EXAMPLE 13

The test specimens without addition of copper described in Example 11 were additionally tested for their colour stability, and in particular:

a. After incorporation (Table 10, column 2)
b. After heat ageing at 149° C (Table 10, column 3)
c. After 1 weeks' treatment with boiling water (Table 10, column 4).

An empirical colour scale was used for Table 10, in which 5 denotes colourless 4 denotes a just perceptible, slight discolouration
3,2,1,<1 denote progressively stronger discolouration.

Table 10

| | Test for Colour Stability (without addition of copper) | | |
|---|---|---|---|
| | Colour Assessment according to Scale 1 – 5 | | |
| Stabiliser No. | After incorporation | After heat ageing at 149° C | Boiling water, 1 week |
| Without additive | 5 | 4 | 4 |
| 1 | 3 | 2 | 3 |
| 2 | 4 | 2 | 2 |
| 3 | 4 | 2 | 3 |
| 4 | 4 | 2 | 3 |
| 8 | 4 | 3 | 4 |
| 11 | 4 | 2 | 3 |
| Comparison Products | | | |
| 32 | 4 – 5 | 2 – 3 | 4 – 5 |
| 33 | 1 | <1 | 2 |
| 34 | 1 | <1 | <1 |
| 35 | <1 | <1 | <1 |
| 36 | <1 | <1 | <1 |
| 37 | 3 – 4 | <1 | 2 |
| 39 | 3 – 4 | <1 | 2 – 3 |
| 40 | <1 | <1 | <1 |
| 41 | 1 | 1 | <1 |
| 42 | 1 | 2 | <1 |
| 43 | 1 | <1 | 2 |

EXAMPLE 14

100 parts of polypropylene (melt index 3.2 g/10 mins, 230° C/2160 g) are thoroughly mixed for 10 minutes in a shaking apparatus with the additives listed in Table 11, in the concentrations indicated.

The mixture obtained is kneaded for 10 minutes in a Brabender plastograph at 200° C, 1.0% by weight of powdered copper (manufactured electrolytically, Merck) is then added, and the whole is intensely mixed for a further 2 minutes at the same temperature. The composition thus obtained is subsequently pressed in a platen press, at 260° C platen temperature, to give 1 mm thick sheets, from which 1 cm wide and 17 cm long strips are punched by means of a punch tool.

The fully stabilised test specimens without addition of copper which are required for comparison purposes are manufactured analogously.

The test of the dependence of the action of the stabilisers on the further additives takes place by heat ageing in a circulating air oven at 149° C. For results, see Table 11, column 4. The oven ageing times of the test specimens without added copper, which are required for comparison, are shown in Table 11, column 3.

Table 11

| Mixture | Additives and Concentration | Oven ageing times, in days, up to incipient decomposition | |
|---|---|---|---|
| | | without copper | with copper |
| 1 | 0.5 Part of Stabiliser 2<br>0.2 Part of Additive A | 18 | 10 |
| 2 | 0.5 Part of Stabiliser 5<br>0.2 Part of Additive B | 25 | 15 |
| 3 | 0.5 Part of Stabiliser 8<br>0.1 Part of Additive C | 22 | 13 |
| 4 | 0.3 Part of Stabiliser 2<br>0.3 Part of Additive D | 20 | 11 |
| 5 | 0.4 Part of Stabiliser 5<br>0.1 Part of Additive E | 22 | 13 |
| 6 | 0.5 Part of Stabiliser 8<br>0.05 Part of Additive E<br>0.15 Part of Additive D<br>0.4 Part of Stabiliser 2 | 21 | 17 |
| 7 | 0.1 Part of Additive B<br>0.3 Part of Additive D<br>0.5 Part of Stabiliser 5 | 38 | 31 |
| 8 | 0.1 Part of Additive C<br>0.3 Part of Additive D<br>0.5 Part of Stabiliser 2 | 50 | 34 |
| 9 | 0.1 Part of Additive A<br>0.3 Part of Additive F | 19 | 14 |

Additives Used:

A: 3-(3,5-Ditert.-butyl-4-hydroxyphenyl)-propionic acid n-octadecyl ester

B: 1,1,3-Tris-(3'-tert.-butyl-4'-hydroxy-5'-methylphenyl

C: 1,3,5-Trimethyl-2,4,6-tris-(3',5'-ditert.-butyl-4'-hydroxybenzyl)-benzene

D: Dilauryl thiodipropionate

E: 3-(3,5-Ditert.-butyl-4-hydroxyphenyl)-propionic acid tetraester of pentaerythritol F: Tris-(nonylphenyl)-phosphite

EXAMPLE 15

100 parts of polypropylene (melt index 3.2 g/10 mins, 230° C/2160 g) are thoroughly mixed for 10 minutes in a shaking apparatus with the additives listed in Table 12, in the concentrations indicated.

The mixture obtained in kneaded for 10 minutes in a Brabender plastograph at 200° C, 0.1% by weight of copper stearate is then added, and the whole is intensely mixed for a further 2 minutes at the same temperature. The composition thus obtained is subsequently pressed in a platen press, at 260° C platen temperature, to give 1 mm thick sheets, from which 1 cm wide and 17 cm long strips are punched by means of a punch tool.

The fully stabilised test specimens without addition of copper stearate which are required for comparison purposes are manufactured analogously.

The effectiveness of the metal deactivator (Stabiliser No. 7) in the test strips containing copper stearate is tested by heat ageing in a circulating air oven at 149° C. For results, see Table 12, column 4. The oven ageing times of the test specimens without added copper stearate, required for comparison, are shown in Table 12, column 3.

Table 12

| Mixture | Additives and Concentration | Days to incipient decomposition without Cu stearate | with Cu stearate |
|---|---|---|---|
| 1 | 0.1 Part of Additive B<br>0.3 Part of Additive D<br>Without metal deactivator | 27 | <<1 |
| 2 | 0.1 Part of Additive B<br>0.3 Part of Additive D<br>0.5 Part of Stabiliser No. 7 | 31 | 23 |

The designation of the additives is the same as in Example 14.

EXAMPLE 16

100 parts of polypropylene (melt index 3.2 g/10 mins., 230° C/2160 g) are thoroughly mixed, in a shaking apparatus, with 0.1 part of 3-(3',5'-ditert.-butyl-4'-hydroxyphenyl)-propionic acid octadecyl ester, 0.3 part of dilauryl thiodipropionate and an additive listed in Table 13 below, in the indicated amount.

The mixture obtained is kneaded for 10 minutes in a Brabender plastograph at 200° C, 1.0% by weight of powdered copper (manufactured electrolytically, Merck) is then added, and the whole is intensely mixed for a further 2 minutes at the same temperature. The composition obtained is subsequently pressed in a platen press, at 260° C platen temperature, to give 1 mm thick sheets, from which 1 cm wide and 17 cm long strips are punched by means of a punch tool.

The effectiveness of the metal deactivators added to the test strips, as a function of the concentration, is tested by heat ageing in a circulating air oven at 149° C. The results are shown in Table 13.

Table 13

(Days to incipient decomposition)

| Stabiliser No. | Amount of Admixed Stabilizer | | |
|---|---|---|---|
|  | 0 Part | 0.2 Part | 0.5 Part |
| 2 | <1 | 18 | 26 |
| 5 | <1 | 14 | 27 |
| 6 | <1 | 13 | 23 |
| 7 | <1 | 15 | 30 |
| 8 | <1 | 15 | 20 |
| 9 | <1 | 18 | 24 |

EXAMPLE 17

100 parts of polypropylene (melt index 3.2 g/10 mins., 230° C/2160 g) are thoroughly mixed for 10 minutes, in a shaking apparatus, with 0.2 part of one of the additives listed in Table 14 below.

The resulting mixture is kneaded for 10 minutes in a Brabender plastograph at 200° C, and the composition thus obtained is subsequently pressed in a platen press at 260° C platen temperature to give 1 cm thick sheets, from which strips of 1 cm width and 17 cm length are punched.

The effectiveness of the additives added to the test strips, in their capacity as antioxidants, is tested by heat ageing in a circulating air oven at 135° C and 149° C, an additive-free test strip serving for comparison. 3 test strips are used of each formulation. The incipient, easily visible decomposition of the test strip is defined as the end point; the results are quoted in days.

Table 14

| Stabiliser No. | Days to incipient decomposition | |
|---|---|---|
|  | 135° C | 149° C |
| Without additive | 1 | ½ |
| 5 | 45 | 3 |
| 20 | 46 | 4 |
| 23 | 48 | 3 |
| Comparison Products | | |
| 32 | 1 | ½ |
| 36 | 1 | ½ |
| 42 | 1 | ½ |
| 43 | 1 | ½ |

EXAMPLE 18

100 parts of polypropylene (melt index 3.2 g/10 mins., 230° C/2160 g) are thoroughly mixed for 10 minutes, in a shaking apparatus, with 0.1 part of 3-(3,5-di-t.butyl-4-hydroxyphenyl)-propionate acid octadecyl ester (Additive A) and 0.3 part of dilauryl thiodipropionate (Additive D) and 0.5 part of an additive listed in Table 15 below.

The resulting mixture is kneaded for 10 minutes in a Brabender plastograph at 200° C, and the composition thus obtained is subsequently pressed in a platen press at 260° C platen temperature to give 1 cm thick sheets, from which strips of 1 cm width and 17 cm length are punched.

The effectiveness of the additives added to the test strips, in their capacity as synergistically acting antioxidants in the presence of the Additives A and/or D, is tested by heat ageing in a circulating air oven at 135° C and 149° C, a test strip which only contains the Additives A and D serving for comparison. 3 test strips of each formulation are employed. The incipient, easily visible decomposition of the test strip is defined as the end point; the results are quoted in days.

Table 15

| Stabiliser No. | Days to incipient decomposition | |
|---|---|---|
|  | 135° C | 149° C |
| Without additive | 90 | 20 |
| 5 | 162 | 59 |
| 7 | 140 | 38 |
| 18 | 140 | 35 |
| 19 | 151 | 42 |
| 21 | 185 | 56 |
| 22 | 170 | 57 |
| 23 | 190 | 54 |
| Comparison Products | | |
| 32 | 85 | 17 |
| 36 | 92 | 17 |
| 42 | 90 | 20 |
| 43 | 86 | 19 |

EXAMPLE 19

100 g of unstabilised high pressure polyethylene powder ("Plastylene" of Messrs. Ethylene Plastique, Mazingarbe, France) are thoroughly mixed dry with 1.0 g of 1,3-bis-(t.butyl-peroxyisopropylbenzene (Perkadox 14 of Messrs. Oxydo GmbH, Emmerich, Germany) and 0.2 g of one of the additives of Table 16 below. The mixture is converted into a homogeneous mass over the course of 10 minutes at 110° C on a friction roll mill. This plastic mixture is pressed in a multi-daylight press at 260° C for 20 minutes to give 1 mm thick sheets, and under these conditions crosslinking of the polymer by the added peroxide occurs. Test specimens of size 10 × 140 mm are punched from the sheets thus manufactured with the aid of a punch tool.

The test specimens are suspended from a V2A-steel stirrup and aged at 120° C in a circulating air oven. After the end of an induction period which is characteristic of the additive, the degraded material drips off; the results are quoted in days.

Table 16

| Stabiliser No. | Days to incipient dripping-off at 120° C |
|---|---|
| Without Stabiliser | 8 |
| 2 | 20 |
| 5 | 25 |
| 9 | 23 |
| Comparison Products | |
| 32 | 8 |
| 43 | 15 |

EXAMPLE 20

Stabilisation of Asbestos-filled Polypropylene 100 parts of polypropylene ("Carlona" of Messrs Shell) are thoroughly mixed with 65 parts of chrysotile asbestos (Messrs Montecatini), 0.5 part of 3-(3,5-di-tert.butyl-4-hydroxyphenyl)-propionic acid octadecyl ester, 1.5 parts of dilauryl thiodipropionate and 0.83 part of an additive listed in Table 17 below.

The resulting mixture is kneaded for 10 minutes in the Brabender plastograph and is subsequently pressed in a platen press at 260° C to give 1 mm thick sheets, from which strips of 1 cm width and 17 cm length are punched.

The effectiveness of the additives added to the test strips is tested by heat ageing in a circulating air oven at 149° C. The easily visible decomposition of the test strip, which manifests itself by chalking of decomposed material, is defined as the end point. The results are quoted in days (Table 17).

Table 17

| Stabiliser No. | Days to decomposition |
|---|---|
| Without stabiliser | 1.5 |
| 2 | 17 |
| 8 | 15 |
| 10 | 18 |
| 21 | 17 |
| 23 | 12 |

EXAMPLE 21 a. Manufacture of the test specimens.

100 parts of unstabilised polybutene-1 in powder form are thoroughly mixed, in a shaking apparatus, with 0.1 part of $\beta$-(3,5-di-tert.butyl-4-hydroxyphenyl)-propionic acid octadecyl ester, 0.3 part of dilauryl thiodipropionate and 0.5 part of Stabiliser No. 2.

This mixture is plasticised and homogenised for 10 minutes in a Brabender plastograph at 200° C, after the end of this time 1 part of powdered electrolytic copper is added and the whole is then mixed for a further 2 minutes at the same temperature. The composition obtained is pressed for 6 minutes in a platen press at 220° C press temperature to give 1 mm thick sheets, and test strips of 1 cm width and 14 cm length are punched therefrom. The test specimens without copper salt required for comparison purposes are manufactured analogously.

b. Testing

The effectiveness of the metal deactivators added to the test specimens containing copper is tested by heat ageing in a circulating air oven at 120° C until the first signs of incipient decomposition of the test specimen are noted. 3 test specimens are employed for each formulation, and their oven life is averaged.

The test specimens which contain the stabiliser as yet show no signs whatsoever of decomposition at a point in time where the unstabilised test specimens have already decomposed completely, as manifests itself by the test specimens becoming very tacky.

EXAMPLE 22

75 parts of unstabilised polypropylene (Vestolen of Messrs "Hüls", Recklinghausen, Germany) are thoroughly mixed for 10 minutes, in a shaking apparatus, with 0.1 part of $\beta$-(3,5-di-tert.butyl-4-hydroxyphenyl)-propionic acid octadecyl ester, 0.3 part of dilauryl thiodipropionate and 0.5 part of the Stabiliser No. 23.

This mixture is introduced into a Brabender plastograph and is plasticised and homogenised at 200° C and 30 revolutions per minute for 5 minutes. Thereafter a mixture of a further 25 parts of polypropylene and 0.1 part of Co-II stearate and Mn-II stearate or Cu-II stearate is added over the course of one minute. After completion of the addition, the torque is continuously recorded in the form of a plastogram for 15 minutes under the conditions of temperature and speed of rotation indicated above. Since the torque melt viscosity and molecular weight are directly related in the sense that under constant conditions a higher torque denotes a higher melt viscosity and hence a higher molecular weight of the polymer, a drop in the torque conversely permits the conclusion that the polymer has degraded.

The plastograms without addition of metal salt and without addition of deactivator, or with metal salts and without addition of deactivator, which are required for comparison purposes, are obtained analogously.

The degradation of the polymer during the kneading period of 15 minutes is expressed in terms of the residual torque at the end of the kneading period, in percent of the initial torque (Table 18, column 5). The effectiveness of the metal activator can be seen from comparing the figures in column 5 for one and the same metal salt with and without Stabiliser No. 23.

Table 18

| Metal salt (0.1%) | Stabiliser No. 23 | Torque in Gram | | |
|---|---|---|---|---|
| | | Start | End | End/Start × 100 |
| Without additive | | 500 | 210 | 42% |
| Co stearate | 0.5% | 485 | 360 | 74% |
| Co stearate | — | 440 | 100 | 23% |
| Mn stearate | 0.5% | 430 | 345 | 80% |
| Mn stearate | — | 360 | 115 | 32% |
| Cu stearate | 0.5% | 430 | 285 | 59% |
| Cu stearate | — | 470 | 210 | 45% |

EXAMPLE 23

100 parts of polypropylene (melt index 3.2 g/10 minutes, 230° C/2160 g) are thoroughly mixed for 10 minutes in a shaking apparatus with the additives listed in Table 19, in the concentrations indicated.

The resulting mixture is kneaded for 10 minutes in a Brabender plastograph at 200° C, 0.1 percent by weight of manganese stearate is then added and the whole is thoroughly mixed for a further 2 minutes at the same temperature. The composition thus obtained is subsequently pressed in a platen press at 260° C platen temperature to give 1 mm thick sheets, from which strips of 1 cm width and 17 cm length are punched by means of a punch tool.

The fully stabilised test specimens, without addition of manganese stearate, which are required for comparison purposes are manufactured analogously.

The effectiveness of the added metal deactivators in the test strips containing manganese stearate is tested by heat ageing in a circulating air oven at 149° C. For results, see Table 19, column 4. The oven ageing times of the test specimens without addition of manganese stearate, which are required for comparison, are shown in Table 19, column 3.

Table 19

| Mixture | Additives and Concentration in parts | Days to incipient decomposition without Mn stearate | with Mn stearate |
|---|---|---|---|
| 1 | 0.1 Additive A 0.3 Additive D Without metal deactivator | 20 | 1 |
| 2 | 0.1 Additive A 0.3 Additive D 0.5 Stabiliser No. 5 | 26 | 12 |
| 3 | 0.1 Additive A 0.3 Additive D 0.5 Stabiliser No. 8 | 27 | 26 |
| 4 | 0.1 Additive A 0.3 Additive D 0.5 Stabiliser No. 9 | 29 | 26 |
| 5 | 0.1 Additive A 0.3 Additive D 0.5 Stabiliser No. 21 | 29 | 25 |

The designation of the additives is the same as in Example 14.

EXAMPLE 24

100 parts of polypropylene (melt index 3.2 g/10 minutes, 230° C/2160 g) are thoroughly mixed for 10 minutes in a shaking apparatus with the additives listed in Table 19, in the concentrations indicated.

The resulting mixture is kneaded for 10 minutes in a Brabender plastograph at 200° C, 0.1 percent by weight of cobalt stearate is then added and the whole is thoroughly mixed for a further 2 minutes at the same temperature. The composition thus obtained is subsequently pressed in a platen press at 260° C platen temperature to give 1 mm thick sheets, from which strips of 1 cm width and 17 cm length are punched by means of a punch tool.

The fully stabilised test specimens, without addition of cobalt stearate, which are required for comparison purposes are manufactured analogously.

The effectiveness of the added metal deactivators in the test strips containing cobalt stearate is tested by heat ageing in a circulating air oven at 149° C. For results, see Table 19, column 4. The test specimens without addition of cobalt stearate, which are required for comparison, are shown in Table 20, column 3.

Table 20

| Mixture | Additives and Concentration in parts | Days to incipient decomposition without Co stearate | with Co stearate |
|---|---|---|---|
| 1 | 0.1 Additive A 0.3 Additive D Without metal deactivator | 20 | 3 |
| 2 | 0.1 Additive A 0.3 Additive D 0.5 Stabiliser No. 5 | 26 | 26 |
| 3 | 0.1 Additive A 0.3 Additive D 0.5 Stabiliser No. 8 | 27 | 25 |
| 4 | 0.1 Additive A 0.3 Additive D 0.5 Stabiliser No. 9 | 29 | 26 |
| 5 | 0.1 Additive A 0.3 Additive D 0.5 Stabiliser No. 21 | 29 | 26 |

The designation of the additives is the same as in Example 14.

What we claim is:

1. A compound of the formula $$\underset{\text{OH}}{\overset{}{\text{(A)}}}-\text{CONHNHCO[XCO]}_n\text{NHNHCO}-\underset{\text{HO}}{\overset{}{\text{(A)}}}$$

wherein
X denotes a direct bond, alkylene of 1 to 8 carbon atoms, m-phenylene or p-phenylene;
$n$ denotes 0 or 1; and
the rings A are each unsubstituted, or one or both rings A are substituted with an hydroxyl, a chlorine atom, an α-methylbenzyl, an alkanoyloxy of 2 to 18 carbon atoms or an alkanoylamino of 2 to 18 carbon atoms; or with one or two alkyl groups each of 1 to 8 carbon atoms, or one or two alkoxy groups each of 1 to 18 carbon atoms.

2. A compound according to claim 1, characterised in that X denotes a direct bond, alkylene with 3 to 8 carbon atoms, m-phenylene or p-phenylene; $n$ denotes 0 or 1; and the rings A are unsubstituted or are each substituted by 1 or 2 alkyl groups with 1 to 8 carbon atoms, an alkoxy with 1 to 18 carbon atoms or a chlorine atom.

3. A compound according to claim 1, characterised in that X denotes alkylene with 3 to 8 carbon atoms; $n$ denotes 0 or 1; and the rings A are unsubstituted.

4. A compound according to claim 1 characterised in that X denotes a direct bond; $n$ denotes 1; and the rings A are each substituted by 1 or 2 alkyl groups with 1 to 8 carbon atoms or an alkoxy with 1 to 8 carbon atoms.

5. A compound according to claim 1, characterised in that X denotes a direct bond, alkylene with 3 to 8 carbon atoms, m-phenylene or p-phenylene; $n$ denotes 1; and the rings A are each substituted by 1 or 2 alkyl groups with 4 to 8 carbon atoms or an alkoxy with 1 to 18 carbon atoms.

6. A composition comprising a polyolefin and from 0.01 to 5% by weight of the polyolefin of a stabilizing compound of claim 1.

7. A composition comprising a polyolefin of an α-olefin polymer and a compound of claim 1.

8. A composition comprising polyethylene and a compound of claim 1.

9. A composition comprising polypropylene and a compound of claim 1.

* * * * *